United States Patent [19]

Bowers et al.

[11] Patent Number: 4,727,874
[45] Date of Patent: Mar. 1, 1988

[54] ELECTROSURGICAL GENERATOR WITH HIGH-FREQUENCY PULSE WIDTH MODULATED FEEDBACK POWER CONTROL

[75] Inventors: William J. Bowers; Phillip D. Hardwick, both of Aurora, Colo.

[73] Assignee: C. R. Bard, Inc., Murray Hill, N.J.

[21] Appl. No.: 649,261

[22] Filed: Sep. 10, 1984

[51] Int. Cl.⁴ .................................... A61B 17/39
[52] U.S. Cl. ...................... 128/303.13; 128/303.14; 128/303.17; 330/207 A; 330/251
[58] Field of Search ............... 128/303.12, 303.13, 128/303.14, 303.15, 303.17, 303.18; 330/251, 207 A

[56] References Cited

U.S. PATENT DOCUMENTS

| | | | |
|---|---|---|---|
| 3,601,126 | 8/1971 | Estes | 128/303.14 |
| 3,675,655 | 7/1972 | Sittner | 128/303.14 |
| 3,854,100 | 12/1974 | Pouzadoux | 330/207 A |
| 3,897,787 | 8/1975 | Ikuno et al. | 128/303.14 |
| 3,897,788 | 8/1975 | Newton | 128/303.17 |
| 3,898,991 | 8/1975 | Ikuno et al. | 128/303.14 |
| 3,939,380 | 2/1976 | Peer | 330/251 |
| 4,021,748 | 5/1977 | Yoshida et al. | 330/207 A |
| 4,038,984 | 8/1977 | Sittner | 128/303.14 |
| 4,173,739 | 11/1979 | Yoshida | 330/207 A |
| 4,188,927 | 2/1980 | Harris | 128/303.14 |
| 4,211,230 | 7/1980 | Woltosz | 128/303.17 |
| 4,281,373 | 7/1981 | Mabille | 128/303.14 |
| 4,347,481 | 8/1982 | Yoshida | 330/207A |
| 4,372,315 | 2/1983 | Shapiro et al. | 128/303.18 |
| 4,390,849 | 6/1983 | Miskin | 330/207 A |
| 4,412,156 | 10/1983 | Ota | 315/308 |
| 4,429,694 | 2/1984 | McGreevy | 128/303.14 |
| 4,438,766 | 3/1984 | Bowers | 128/303.14 |
| 4,439,738 | 3/1984 | Atherton | 330/207 A |
| 4,474,179 | 10/1984 | Koch | 128/303.17 |
| 4,569,345 | 2/1986 | Manes | 128/303.14 |

FOREIGN PATENT DOCUMENTS

| | | |
|---|---|---|
| 0136855 | 4/1986 | European Pat. Off. . |
| 1519225 | 6/1978 | United Kingdom . |
| 2085243 | 4/1982 | United Kingdom . |
| 2108786 | 5/1983 | United Kingdom . |

Primary Examiner—Lee S. Cohen
Assistant Examiner—David Shay
Attorney, Agent, or Firm—John R. Ley

[57] ABSTRACT

A pulse width modulation technique regulates the output power of each cycle of a radio frequency surgical signal of an electrosurgical generator. The delivered power of the surgical signal is determined by multiplying the sensed current and the sensed voltage of the surgical signal. An error signal is established by the difference of the actual delivered power with respect to a selected desired output power. The error signal is operatively utilized to modulate the pulse width of each driving pulse which creates the cycles of the surgical signal. Limits on the sensed voltage and sensed current signals are established to limit the output characteristics of the surgical signal. A minimum current limit signal is utilized to limit the maximum output voltage into relatively high impedances. A minimum voltage limit signal is utilized to limit the maximum output current into relatively low impedances. Very rapid response times and very effective power regulation even into relatively high impedance tissues are possible with the pulse width modulation technique. The risks and problems associated with open circuit flashing, alternate path burns and closed circuit shorting are substantially reduced or eliminated.

34 Claims, 19 Drawing Figures

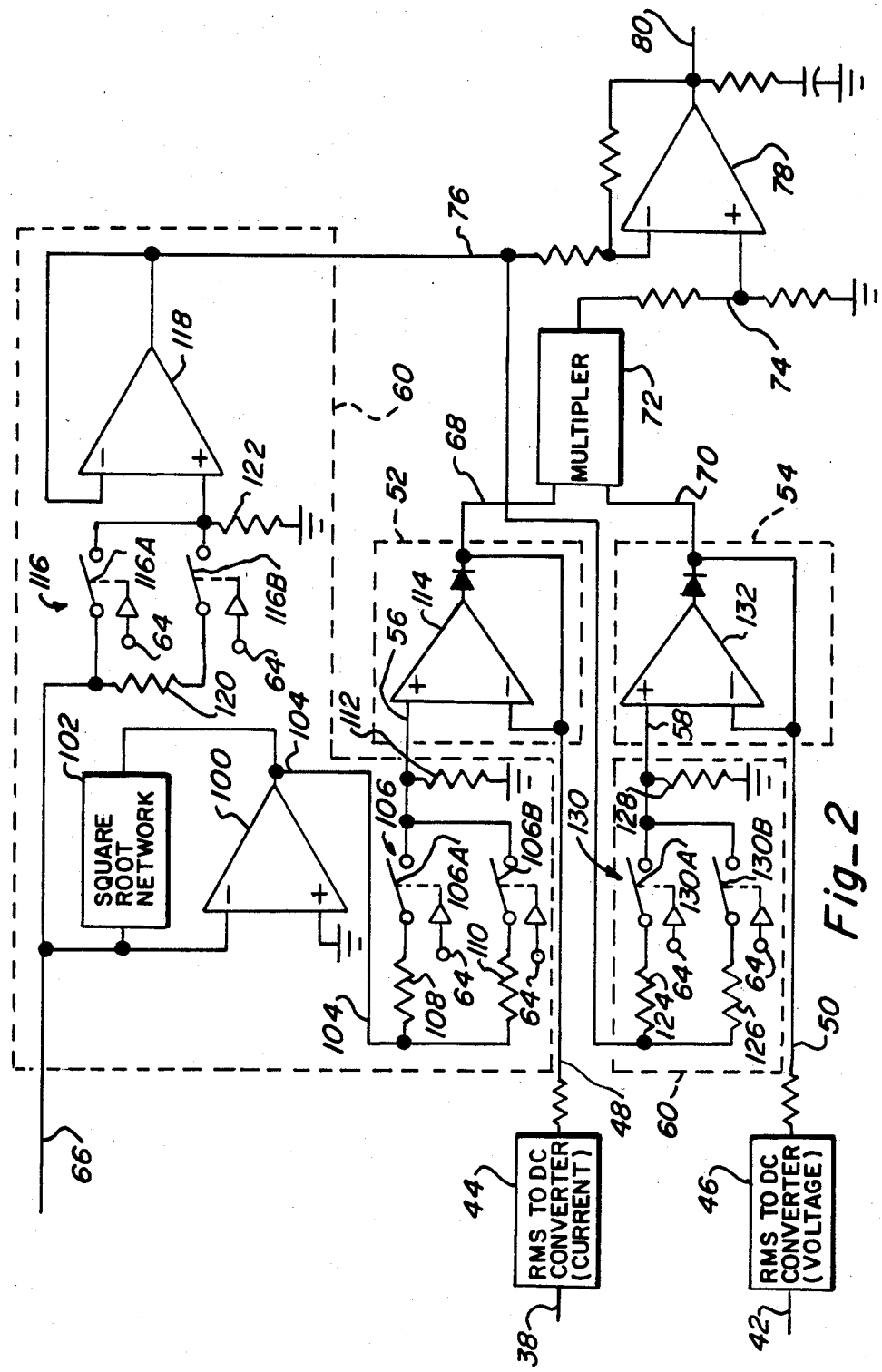
Fig_2

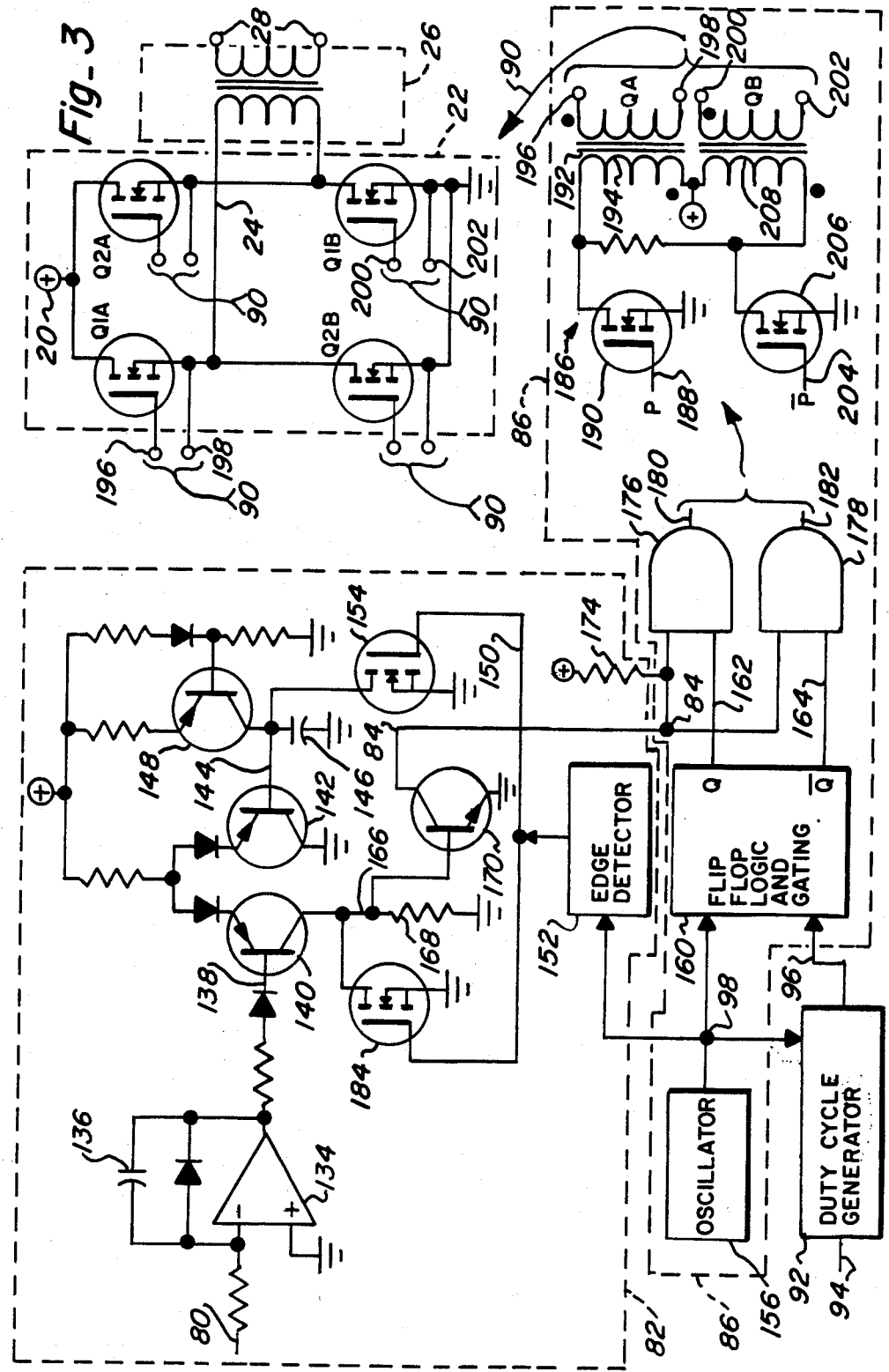
Fig_3

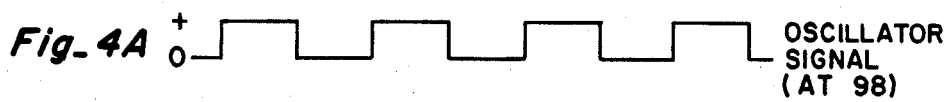
Fig.4A — OSCILLATOR SIGNAL (AT 98)
Fig.4B — PULSE PHASE 1 SIGNAL (AT 162)
Fig.4C — PULSE PHASE 2 SIGNAL (AT 164)
Fig.4D — EDGE SIGNAL (AT 150)
Fig.4E — RAMP SIGNAL (AT 144)
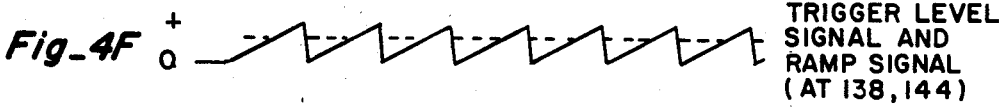
Fig.4F — TRIGGER LEVEL SIGNAL AND RAMP SIGNAL (AT 138,144)
Fig.4G — TERMINATION SIGNAL (AT 166)
Fig.4H — PULSE WIDTH CONTROL SIGNAL (AT 84)
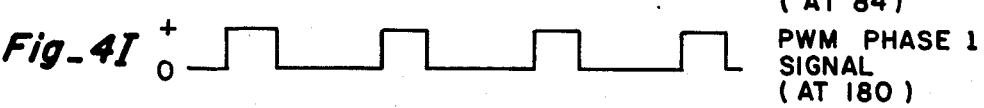
Fig.4I — PWM PHASE 1 SIGNAL (AT 180)
Fig.4J — PWM PHASE 2 SIGNAL (AT 182)
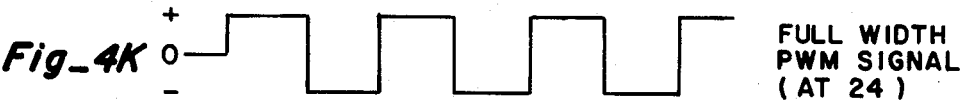
Fig.4K — FULL WIDTH PWM SIGNAL (AT 24)
Fig.4L — PWM SIGNAL (AT 24)
Fig.4M — SURGICAL SIGNAL (AT 32)

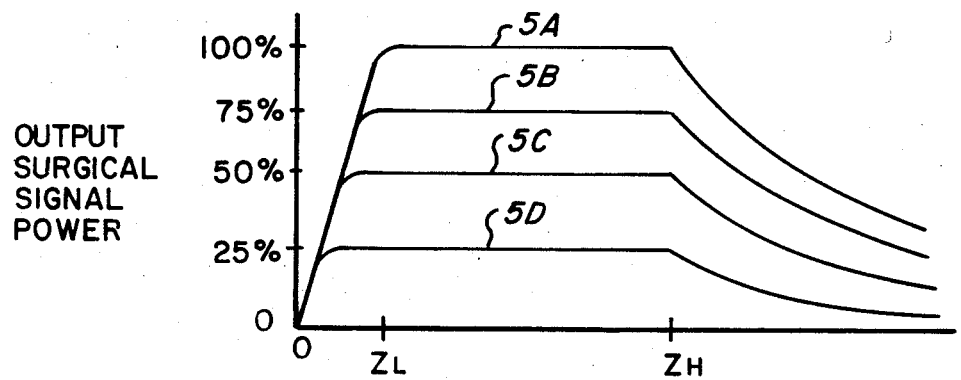
Fig_5
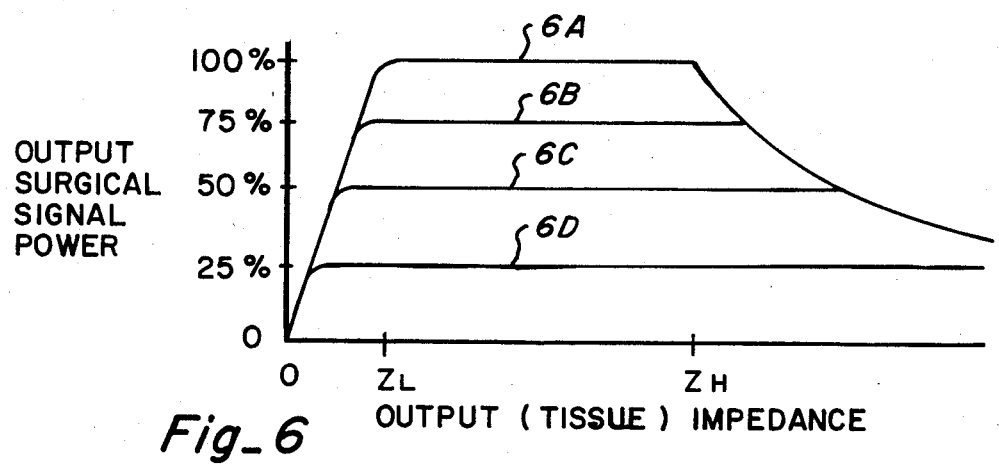
Fig_6
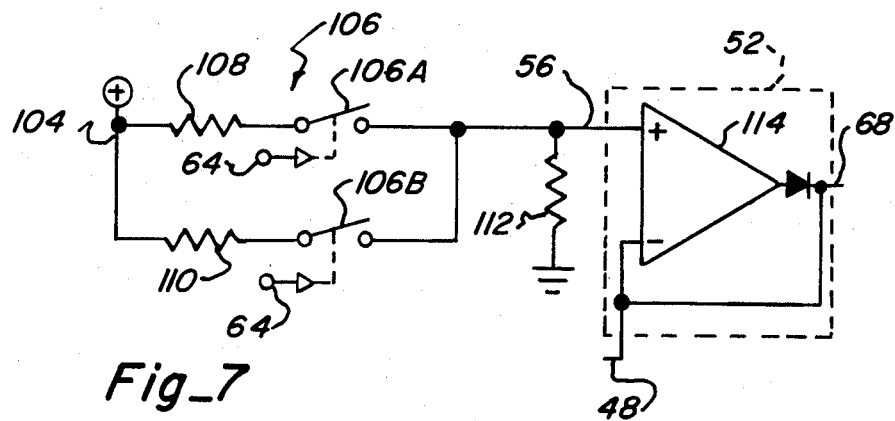
Fig_7

ELECTROSURGICAL GENERATOR WITH HIGH-FREQUENCY PULSE WIDTH MODULATED FEEDBACK POWER CONTROL

This invention pertains to an electrosurgical generator having an improved output power regulation capability as a result of a closed loop feedback power control network utilizing pulse width modulation at the frequency of, and to control the energy content of, each cycle of the high-frequency surgical signal, among other improved features.

By use of an electrosurgical generator in a surgical procedure, it is possible for the surgeon to cut, to blend or cut with hemostasis, or to purely coagulate. The surgeon can quickly select and change the different modes of operation as the surgical procedure progresses. In each mode of operation, it is important to regulate the electrical power delivered to the patient to achieve the desired surgical effect. Applying more power than is necessary will result in unnecessary tissue destruction and prolong healing. Applying less than the desired amount of electrical power will usually inhibit the surgical procedure. Different types of tissues will be encountered as the procedure progresses and each different tissue will usually require more or less power due to a change in inherent tissue impedance. Accordingly, all successful types of electrosurgical generators employ some type of power regulation in order to control the electrosurgical effects desired by the surgeon.

Two types of power regulation are conventional in previous electrosurgical generators. The most common type controls the DC power supply of the generator. This type of power regulation limits the amount of power absorbed from the conventional AC power line to which the generator is connected. A feedback control loop compares the actual power supplied by the power supply to a desired power setting in order to achieve regulation. Another type of power regulation in previous electrosurgical generators involves controlling the gain of the high-frequency or radio frequency amplifier. A feedback control loop compares the output power supplied from the RF amplifier to a desired power level, and the gain is adjusted accordingly.

While both known types of power regulation have achieved moderate success, there nevertheless have been certain undesirable characteristics associated with each. One undesirable characteristic involves the response time for regulation. The impedance of the different tissues encountered during the surgical procedure can fluctuate substantially. In moving from a high impedance tissue to a low impedance tissue, the low impedance tissue may be unnecessarily destroyed or damaged before the electrosurgical generator can reduce the output power to a level compatible with the low impedance tissue. Similarly, when a high impedance tissue is encountered, the output power from the generator may be momentarily insufficient to create or continue the precise surgical effect desired by the surgeon. Precise execution of the surgical procedure becomes difficult or impossible.

Another problem of power regulation in previous electrosurgical generators has resulted in large measure because such previous generators have been designed to attain maximum power transfer to intermediate impedance ranges. As with any amplifier, an electrosurgical generator will achieve maximum power transfer when its internal impedance is equal to the output load impedance to which the generator is connected. At high impedances, the power delivered inherently rolls off because of the difference in load impedance compared to the internal impedance. To compensate, the surgeon increases the power setting to a higher level than necessary. As soon as the incision progresses through the high impedance tissue, the output power is too great and tissue destruction or undesirable surgical effects result. Making the initial incision is an example. The skin includes a relatively large percentage of dead cells and cells which contain considerably less moisture than other cells in tissues beneath the skin, which increases its impedance compared to the impedance of the tissues below the skin. A higher power setting is therefore required for the initial incision. However, as soon as the incision is made, a reduced amount of power is all that is necessary. With typical previous electrosurgical generators, the initial incision was deeper than desired because the active electrode, i.e., the electrosurgical instrument, went deeper than the surgeon desired due to the excessive amount of power delivered. The surgeon usually desires to control the depth of the incision and conduct the surgical procedure in controlled depth levels. If the power regulation is not reliable, a deeper incision in certain areas may result in undesired bleeding or other undesirable surgical effects. It is for this reason that most surgeons generally prefer to make the initial incision using a conventional scalpel, rather than using the active electrode of an electrosurgical generator.

Another power-regulation-related problem of previous electrosurgical generators is open circuit flashing just prior to the commencement of the surgical procedure. Before the electrosurgical procedure commences, no output power is supplied due to the open circuit condition. The regulation circuitry attempts to compensate by creating maximum power delivery situation. As soon as the active electrode is moved into operative distance from the tissue, an immediate flash or arcing is caused by the relatively high voltage which exists due to the maximum power delivery capability created by the power regulation circuitry. Although continual arcing is desired in the coagulation (fulguration) mode of operation, it is usually undesirable in the other modes of operation. The power regulation circuitry eventually compensates for the excessive power and reduces it. Nonetheless, the initial arcing or flash usually causes excessive tissue destruction and other undesirable tissue effects. The flash and excessive tissue destruction can occur anytime the surgeon moves the active electrode to the tissue.

Open circuit or excessively high output impedance conditions also increase the risks of alternate path burns to the patient. Alternate path burns are burns created by current flowing from the patient to some surrounding grounded conductive object such as the surgical table, rather than returning to the electrosurgical generator through the patient plate, i.e., the inactive electrode. Alternate path burns usually are caused by radio frequency leakage currents created by the high-frequency surgical signal flowing through stray capacitances between the patient and an adjacent grounded object. Reducing the output voltage under open circuit or high impedance conditions reduces the magnitude of and possibility for radio frequency leakage currents.

Another power-regulation-related problem of previous electrosurgical generators relates to shorting the output terminals of the generator. Human nature being what it is, one usual, although not recommended, technique of quickly determining whether an electrosurgical generator is operating is to simply short the two output electrodes and observe an electrical spark. A not unusual result of such shorting is the destruction of the power supply in the generator. The generator is forced to quickly attempt to regulate from a high power open circuit condition to a short circuit low impedance condition. Due to the limitations on regulating capability, the electrical power components of the power supply are usually overdriven and are quickly destroyed before compensation can occur.

BRIEF SUMMARY OF THE INVENTION

The present invention teaches an improved technique of regulating the output power of an electrosurgical generator which obtains a more rapid response time to obtain better and constant power regulation even into relatively high and low impedance loads, and which limits the output current and voltage to avoid or reduce the problems of and risks associated with open circuit flashing, alternate path burns and short circuit destructive currents.

In accordance with one of its major aspects, each cycle of a high-frequency surgical signal supplied by the electrosurgical generator is regulated in power content by modulating the width of driving pulses of energy. The driving pulses operatively create each cycle of the surgical signal. A closed loop feedback power control arrangement creates a delivered power signal representative of the power content of the surgical signal by sensing the current and voltage associated with the surgical signal. The width of each driving pulse of energy is modulated in accordance with a relationship of the delivered power signal relative to a selected desired output power signal to thereby regulate the power content of the surgical signal to an amount substantially equivalent to the desired amount of output power. Since each cycle of the surgical signal is regulated in power content, very rapid power regulation response times are possible. At desired output power levels which are less than the full capacity of the electrosurgical generator, power regulation and control is attained even into relatively high impedance tissues, unlike previous electrosurgical situations where power roll-off and lack of regulation typically occurred.

In accordance with another improved aspect, a voltage or a current limit signal is substituted for the actual sensed voltage or current signal in order to, respectively, limit the maximum output current of the generator into relatively low impedances and limit the maximum output voltage of the generator into relatively high impedances. Limiting the maximum output voltage into relatively high impedances attains the desirable effects of reducing or eliminating flash and undesirable arcing, of achieving beneficial electrosurgical effects on the tissue, and of reducing the risk of alternate path burns. Limiting the maximum output current into relatively low impedances has the beneficial effect of preventing destructively high currents, even when short circuiting of the output terminals or electrosurgical electrodes of the generator.

The actual aspects of the present invention are defined in the appended claims. A more complete understanding of the improvements of the electrosurgical generator can be obtained from the following description of a preferred embodiment taken in conjunction with the drawings.

DETAILED DESCRIPTION OF THE DRAWINGS

FIG. 2 is an expanded block and schematic diagram of certain portions of FIG. 1.

FIG. 3 is an expanded block and schematic diagram of certain portions of FIG. 1.

FIGS. 4A, 4B, 4C, 4D, 4E, 4F, 4G, 4H, 4I, 4J, 4K, 4L and 4M are waveform diagrams illustrating signals present at certain locations in the diagrams shown in FIGS. 1 and 3.

FIG. 5 is a graph of output surgical signal power relative to output (tissue) impedance illustrating power regulation curves attained by the circuit arrangement illustrated in FIG. 2.

FIG. 6 is a graph of output surgical signal power relative to output (tissue) impedance of the electrosurgical generator when modifications to a portion of the circuit shown in FIG. 2 are made.

FIG. 7 is a schematic diagram of a circuit intended to replace a portion of a circuit shown in FIG. 2.

DESCRIPTION OF THE PREFERRED EMBODIMENT

Figure 1:
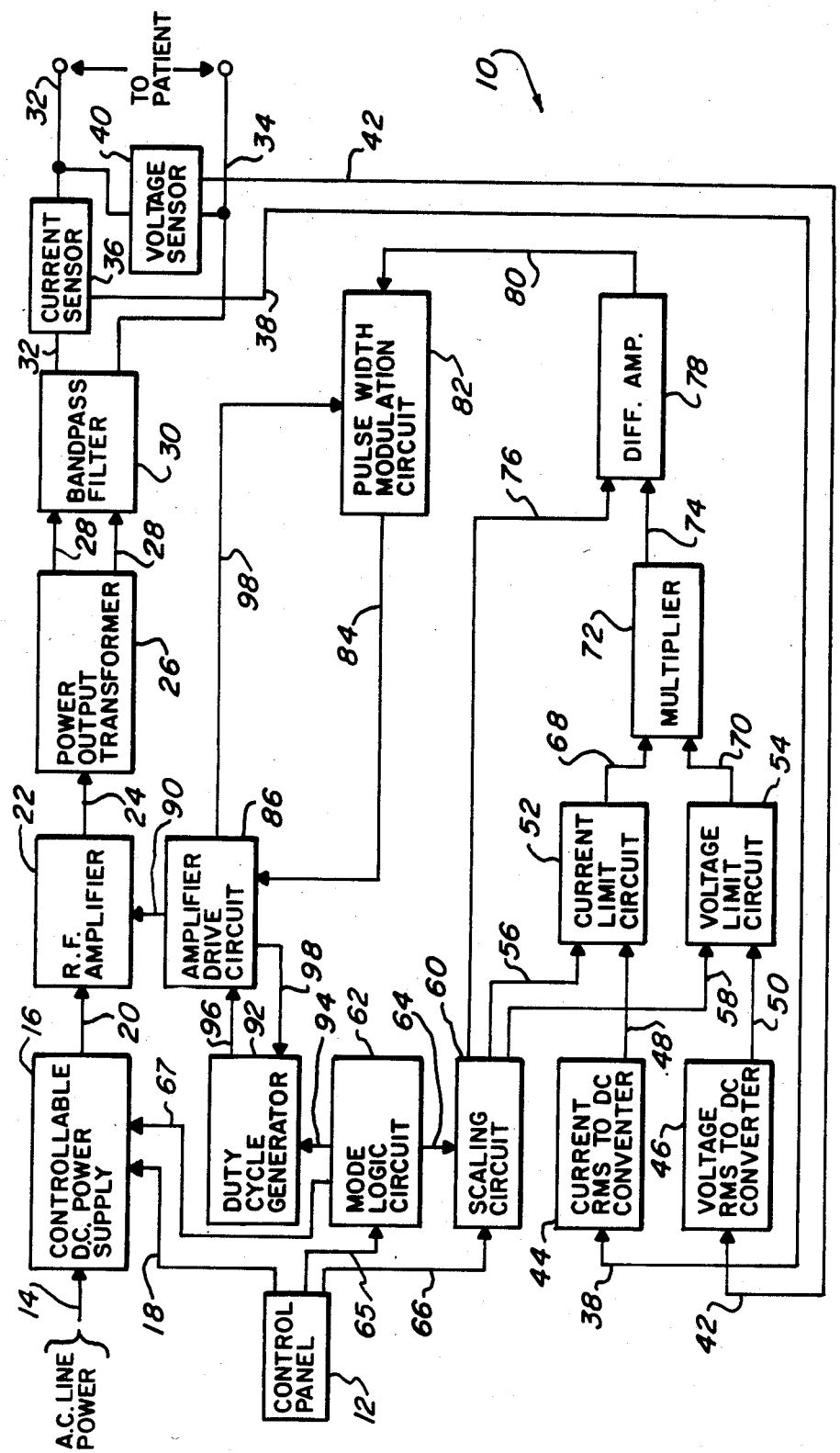
FIG. 1 is a block diagram of the electrosurgical generator of the present invention.

A preferred embodiment of the electrosurgical generator of the present invention is shown and referenced 10 in FIG. 1. A control panel 12 of the generator 10 includes the typical switches and other control devices for controlling the mode of operation of the generator 10 and the amount of power to be delivered in each mode. In addition, the control panel 12 may include means for adjusting the blend or relative amounts of cutting and hemostasis which occurs during the cutting with hemostasis mode of operation. AC power is supplied to the generator 10 from a conventional AC power line 14. A controllable DC power supply 16 converts the AC power from the line 14 to a DC power level at 20. A power output control signal is supplied at 18 from the control panel 12 to control and generally limit the DC power output at 20 from the supply 16 according to the amount of power desired. The output power at 20 from the supply 16 is applied to a conventional high frequency or radio frequency electrosurgical amplifier 22. The amplifier 22 converts the DC power at 20 into a periodic pulse width modulated signal at 24. A power transformer 26 receives the pulse width modulated signal at 24 and converts it to an alternating or AC pulse width modulated signal at 28.

The alternating pulse width modulated signal at 28 is applied to a band pass filter 30 which has a band pass characteristic only at the predetermined high or radio frequency of the surgical signal delivered by the generator. The filter supplies a high frequency surgical signal at 32. The surgical signal 32 creates the surgical effect or procedure. The frequency of the surgical signal is sufficiently high to avoid stimulating nerves, for example five hundred kilohertz. The filter 30 eliminates any higher order harmonics created by the amplifier 22 or the transformer 26 to reduce the risk of alternate path (leakage capacitance) burns to the patient. The filter 30 also inhibits the existence of circulating DC currents created by rectification effects of the tissue. The filter 30 converts the alternating signal at 28 to a sinusoidal waveform due to the effects from the passive reactive elements of the filter. The high-frequency surgical signal is applied to conductor 32, which is connected to the active electrode used by the surgeon. Conductor 34 is the reference potential conductor for the high-frequency surgical signal and it is connected to the patient plate or inactive electrode upon which the patient is positioned. When a bipolar electrosurgical instrument is used, both conductors 32 and 34 are connected to the instrument. Although not shown, output isolation capacitors can be placed in conductors 32 and 34 to also inhibit the DC circulating currents.

A current sensor 36 is connected in series in the conductor 32 for the purpose of deriving an instantaneous current sense signal at 38 which is related to the instantaneous magnitude of current flowing in the conductor 32. A voltage sensor 40 is electrically connected between the conductors 32 and 34 for the purpose of deriving an instantaneous voltage sense signal at 42 representative of the instantaneous voltage existing between the conductors 32 and 34. Accordingly, both the instantaneous output current and voltage of the high-frequency surgical signal are sensed at a point in the generator 10 where the surgical signal is delivered. An accurate indication of the amount of instantaneous output current and voltage applied to the tissue is thereby obtained. More exact sense signals are obtained as compared to some prior arrangements of sensing either current or voltage or both as they are applied to the input terminal to an amplifier or to the input terminal of an output transformer or the like. These prior arrangements suffer the substantial disadvantages of failing to consider losses and inefficiencies inherent in elements such as the amplifiers and transformers.

To achieve individual pulse and cycle energy regulation of the high-frequency surgical signal, the current and voltage sense signals at 38 and 42 are applied to RMS to DC converters 44 and 46, respectively. The converters 44 and 46 convert the input sense signals to an RMS value represented by a DC output signal. Accordingly, the signal present at 48 is a DC signal which represents the RMS value of the actual output current of the surgical signal, and the signal present at 50 is a DC signal which represents the RMS value of the actual output voltage of the surgical signal applied to the patient. Converting the instantaneous current and voltage sense signals to RMS value gives a true and accurate representation of the amount of current and voltage actually delivered in the surgical signal, unlike other prior techniques not involving RMS conversion.

The RMS current-related signal at 48 is applied to a current limit circuit 52, and the RMS voltage-related signal at 50 is applied to a voltage limit circuit 54. Minimum current limit and minimum voltage limit signals at 56 and 58 are supplied to the limit circuits 52 and 54, respectively, from a scaling circuit 60. The scaling circuit 60 is operatively controlled by a mode logic circuit 62 which supplies scaling control signals at 64 to the scaling circuit 60. The scaling circuit 60 is also operatively controlled by a selected power signal 66 supplied by the control panel 12. The mode logic circuit 62 is controlled by mode control signals applied at 65 from the control panel 12. The mode control signals at 65 operatively establish the mode of operation of the generator 10. The mode logic circuit 62 also supplies a control signal at 67 to the power supply 16 to control the level of DC power at 20 in accordance with the mode of operation selected.

The magnitude of the minimum current limit signal at 56 and the magnitude of the minimum voltage limit signal at 58 are established by the mode of operation of the generator 10, and in response to the magnitude of the selected power signal applied at 66. The minimum current limit signal at 56 represents a minimum amount of current which is considered to be delivered into high impedances, and has the effect of limiting the maximum voltage of the surgical signal applied to high impedances. The minimum voltage limit signal at 58 represents that magnitude of output voltage which is considered to be delivered into low impedances, and has the effect of limiting the maximum current of the surgical signal into low impedances.

The limit circuit 52 compares the minimum current limit signal at 56 with the signal at 48 representative of the actual amount of current delivered in the surgical signal. So long as the RMS current-related signal at 48 exceeds the minimum current limit signal at 56, the current limit circuit 52 supplies a current delivered signal at 68 which corresponds to the signal at 48. Similarly, the voltage limit circuit 54 compares the minimum voltage limit signal at 58 with the signal at 50 representative of the actual delivered voltage of the high-frequency surgical signal. So long as the RMS voltage-related signal at 50 exceeds the minimum voltage limit signal at 58, a voltage delivered signal is present at 70 which corresponds to the signal at 50. Should either the RMS current-related signal or the RMS voltage-related signal fall below the levels of the signals at conductors 56 and 58, respectively, the minimum current limit signal or the minimum voltage limit signal is clamped and supplied at 68 or 70, respectively, as the current delivered signal or the voltage delivered signal. Accordingly, the current delivered signal at 68 is the greater one of either the RMS current-related signal at 48 or the minimum current limit signal present at 56. Similarly, the voltage delivered signal at 70 is the greater of either the RMS voltage-related signal at 50 or the minimum voltage limit signal at 58. Limiting the current delivered signal at 68 to a value no less than that signal at 56 has the effect of holding the output voltage of the surgical signal to a predetermined maximum level at high impedances. Limiting the voltage delivered signal at 70 to the minimum amount established by the signal at 58 has the effect of limiting the output current of the surgical signal at low impedances to a preestablished and safe maximum.

A signal representative of the delivered power is created by a conventional analog multiplier 72, by multiplying the current delivered signal at 68 and the voltage delivered signal at 70. The multiplier 62 supplies a delivered power signal at 74.

The scaling circuit 60 also supplies a signal at 76 representative of a desired output power level of the surgical signal. The scaling circuit 60 establishes the desired output power signal at 76 in accordance with the selected power signal at 66 from the control panel 12, and in accordance with scaling control signals at 64 supplied by the mode logic circuit 62 according to the selected mode of operation.

The desired output power signal at 76 and the delivered power signal at 74 are compared at a differential amplifier 78 and an error signal is supplied at 80. The error signal at 80 represents the difference in magnitude between the delivered power and the desired power. A pulse width modulation circuit 82 receives the error signal at 80 and utilizes the error signal to create a pulse width control signal at 84.

An amplifier drive circuit 86 receives the pulse width control signal at 84 and creates a drive signal at 90. The drive signal is defined by a series of driving pulses delivered at a predetermined frequency to establish the predetermined frequency of the surgical signal. The width or time duration of each driving pulse is controlled by the pulse width control signal at 84. The drive signal at 90 controls the operation of the amplifier 22. Each driving pulse establishes the width and hence energy content of each pulse of the pulse width modulated signal at 24. The width of each pulse of the pulse width modulated signal regulates the output power of each cycle of the surgical signal. Thus, this power is ultimately controlled by the pulse width control signal at 84.

A duty cycle generator 92 is controlled by a signal at 94 from the mode logic circuit 62. A duty cycle signal at 96 from the duty cycle generator 94 also controls the amplifier drive circuit 86. A duty cycle type of operation is typically established in the cut with hemostasis and the coagulation modes of operation of the generator 10. The duty cycle signal at 96 causes the amplifier drive circuit 86 to control the delivery of pulses in the driving signal at 90 in a periodic duty cycle fashion in accordance with the mode of operation. In the cut mode of operation, the surgical signal is a continuous sinusoidal wave and the duty cycle generator 92 is inoperative. A synchronization or oscillator signal is supplied at 98 by the amplifier drive circuit 86 to cause the pulse width modulation circuit 82 to synchronously respond at the same frequency as the frequency of the driving pulses of the drive signal at 90.

It is appreciated, therefore, that the pulse width control signal at 84 is derived by a comparison of the delivered power signal to the selected desired output power signal. Minor fluctuations in the output level at 20 of the controllable DC power supply 16 become largely insignificant because the primary or refined power control is obtained by pulse width modulation. The number of components of the main DC power supply can be reduced, as well as the cost of the power supply and the size and weight of the electrosurgical generator. For example, the typical expensive, heavy and costly line transformer of the typical previous electrosurgical generator power supply can be essentially eliminated and replaced by controllable phase angle switching devices for controlling the amount of power conducted from the AC line directly to the typical rectifiers and filter capacitors. A power supply of reduced cost, components, size and weight results, but it is still operatively sufficient to obtain a sufficient amount of coarse power regulation at the power supply 16 to allow the pulse width modulation technique to achieve final precise power regulation.

Because of each of the driving pulses at the predetermined high frequency is width and energy modulated, the power regulation response times are rapid. The surgeon can more accurately and precisely control the surgical procedure as it progresses, and many of the previous typically-occurring undesirable effects caused by tissue impedance changes can be substantially reduced or eliminated.

Details of the RMS to DC converters 44 and 46, the limit circuits 52 and 54, the multiplier 72, the comparator 78, and the scaling circuit 60 are shown in FIG. 2.

The selected power signal at 66 is derived by adjustment of a conventional potentiometer (not shown) at the control panel 12 (FIG. 1). The selected power signal at 66 is a voltage signal which represents the desired level of power. The selected power signal is utilized to create the minimum current limit signal at 56 which is applied to the limit circuit 52. The minimum current limit signal at 56 is created by applying the selected power signal at 66 to an operational amplifier (op amp) referenced 100. A conventional square root network 102 is connected between the output terminal of the op amp 100 and its input terminal which receives the selected power signal at 66. The output signal from the op amp 100, present at 104, generally represents the square root of the selected power signal at 66. The square root of the selected power signal is desired because the minimum current limit signal at 56 operatively acts to control and limit the output voltage of the surgical signal to a maximum constant level into high impedances. The output voltage of the surgical signal is related to the output power by a squared function for a given impedance or resistance load and thus the output power is related to the output voltage by a square root function. Accordingl.y, since the selected power signal at 66 represents power, its square root relates to an output voltage of the surgical signal for a given impedance or resistance load. The signal at 104 is thus a non-linear (square root) function of the selected power signal at 66.

A scaling function is performed on the signal at 104 by a conventional analog switch 106 and a resistor-divider network. The scaling control signals from the mode logic circuit 62 (FIG. 1) are supplied at 64 to selectively control a conventional analog switch 106 of the scaling circuit 60. The scaling control signals comprise a plurality of individual signals, but for simplicity of description each is referenced at 64. Upon application of a scaling control signal at 64, one of the switches 106A or 106B is closed and a voltage divider network is established between one of the resistors 108 or 110 and the resistor 112. The one of the switches 106A or 106B which is closed depends on the mode of operation of the electrosurgical unit selected by the surgeon. For simplicity of description, only two different scaling functions are obtained from the analog switch 106, although in reality a greater number will be provided in accordance with at least the three different modes of operation of the electrosurgical generator. The level of the limit signal is established by the resistor-divider network.

The minimum current limit signal at 56, which limits the maximum output voltage of the surgical signal, is supplied to the positive input of a precision clamp 114 of the limit circuit 52. The RMS current-related signal at 48 is supplied to the negative input of the clamp 114. So long as the RMS current-related signal at 48 exceeds the minimum current limit signal at 56, the RMS current-related signal at 48 is present at 68 as the current delivered signal. However, should the RMS current-related signal at 48 fall below the minimum current limit signal at 56, the clamp 114 supplies the minimum current limit signal at 68 as the current delivered signal. Thus, even though the electrosurgical generator may actually be supplying less than the predetermined minimum current in the surgical signal, the power regulation circuitry operates on the artificial basis that the minimum current is supplied. The maximum output voltage of the surgical signal is limited accordingly. The effect is that the actual output power of the electrosurgical generator rolls off or decreases into high impedances because the power regulation feedback circuit operates on the artificial basis of a constant output current delivery at high impedances, due to the introduction of the minimum current limit signal at 56 into the power calculation at the multiplier 72 instead of the RMS current-related signal at 48.

Examples of the actual power roll-off in the surgical signal from the electrosurgical generator at high impedances, by using a minimum current limit signal related to the square root of the selected power signal or level, are shown by the curves 5A, 5B, 5C and 5D in FIG. 5. The four curves 5A, 5B, 5C and 5D represent selected power settings for the electrosurgical generator of one hundred percent, seventy-five percent, fifty percent and twenty-five percent, respectively. The curve 5A therefore represents the maximum power output capability of the electrosurgical generator. By deriving the minimum current limit signal from the square root of the selected power signal, as has been described and shown in FIG. 2, the roll-off in power regulation capability at any selected power level occurs at approximately the same predetermined relatively high impedance designated ZH in FIG. 5 and occurs non-linearly generally like that inherent non-linear power roll-off at maximum power delivery capacity.

In many applications, it is desirable to avoid power roll-off at high impedances when the electrosurgical generator is operating at less than its maximum selected power capability. To avoid the roll-off in power shown in FIG. 5 at the high impedances, when operating the generator at less than its maximum output power level, the current limit circuit 52 is eliminated and the minimum current limit signal at 56 is not created. Instead, the RMS current-related signal 48 is directly supplied as the current delivered signal at 68 to the multiplier. Power regulation curves 6A, 6B, 6C and 6D illustrated in FIG. 6 result. Curve 6A represents the inherent maximum power delivery capacity of the generator and is essentially the same as curve 5A in FIG. 5. Curves 6B, 6C and 6D represent the power output at seventy-five percent, fifty percent and twenty-five percent of maximum capacity, respectively. At the less-than-maximum capacity, constant or regulated power is delivered into impedances greater than impedance ZH. Regulated power is delivered until the maximum delivery capacity of the generator is reached, i.e., when curves 6B, 6C or 6D intersect curve 6A, at which point power roll-off occurs because the inherent maximum power generation capacity is reached.

Attaining constant power regulation at high impedances at less than maximum selected power output levels is an important improvement in electrosurgery. It has been discovered that many beneficial effects occur as a result of constant power regulation as the tissue impedance increases or when relatively high impedance tissues are encountered during the electrosurgical procedure. A better surgical effect can be created by the surgeon as a result of this constant power regulation. The pulse width modulation technique is more effective for power regulation into the higher load impedances than known prior power regulation techniques.

In some other situations, it is desirable to retain the limit circuit 52 and generate a minimum current limit signal at 56, but modify the value and relationship of the minimum current limit signal to other signals and operative constraints of the generator. For example, it may be desirable to limit the maximum output voltage of the surgical signal to prevent or reduce flash and the risk of alternate path burns but still obtain constant power regulation into high impedance tissues. A circuit portion shown in FIG. 7 is an example of a circuit which will create a constant minimum limit signal at 56. With reference to FIG. 2, the op amp 100 and the square root network 102 are eliminated, and the circuit portion shown in FIG. 7 is substituted. The signal at 104 is directly connected to a constant positive circuit voltage. The resistive network established by the resistors 108, 110 and 112, and the selective closure of one of the switches 106A or 106B establishes the minimum current limit signal at 56. An example of a circuit which creates a limit signal which varies linearly with respect to another variable signal is illustrated by the following description of the voltage limit circuit 54, with the understanding that the same principle can be applied in the creation of minimum current limit signals.

Various types of minimum current limit signals at 56 have thus been described. A minimum current limit signal which varies in non-linear relationship (e.g., a square root relationship) to a variable signal (e.g., the selected power signal at 66) is derived from the circuit portion illustrated in FIG. 2. A constant minimum current signal regardless of power setting is derived from the circuit portion illustrated in FIG. 7. A linearly changing minimum current limit signal is illustrated by the following description of the derivation of the minimum voltage limit signal at 58. From these examples, it is apparent that circuits for generating minimum specially tailored current limit signals are possible. Such circuits could regulate the power output capability at less than maximum power settings to accommodate particular types of surgical procedures, should it be discovered that particular types of surgical procedures require specifically tailored power regulation curves at particular impedances.

To obtain the desired output power signal at 76 as shown in FIG. 2, the selected power signal at 66 is scaled as a result of an analog switch 116 operatively controlled by the scaling control signals applied at 64, in accordance with the selected mode of operation. Closure of switch 116A causes the full selected power signal to be applied to the op amp 118 which functions as a buffer. The desired power output signal at 76 is the same as the selected power signal at 66 under such circumstances. Closure of switch 116B establishes a voltage divider network comprising resistors 120 and 122 to reduce the magnitude of the selected power signal at 66 and cause the desired power output signal at 76 to correspond to this reduced level.

The minimum voltage limit signal at 58 is derived from the desired output power signal at 76. The desired output power signal at 76 is selectively switched into a voltage dividing network comprising resistors 124, 126 and 128 by an analog switch 130 of the scaling circuit 60. The switches 130A and 130B are selectively controlled by the scaling control signals applied at 64. The minimum voltage limit signal at 58, which operatively controls the maximum output current of the surgical signal, is linearly related to the desired output power signal at 76 due to the effects of the voltage divider network.

An op amp 132 functions as a precision clamp in the limit circuit 54. The minimum voltage limit signal at 58 is applied to the positive terminal of the op amp 132 and the RMS voltage-related signal at 50 is applied to the negative terminal. So long as the RMS voltage-related signal at 50 is greater than the minimum voltage limit signal at 58, the RMS voltage-related signal is supplied as the voltage delivered signal at 70. However, should the RMS voltage-related signal at 50 fall below the minimum voltage limit signal at 58, the minimum voltage limit signal is supplied as the voltage delivered signal at 70.

By introducing the minimum voltage limit signal as an artificial substitute for the RMS voltage-related signal, the maximum output current of the surgical signal is limited to a maximum value even though the output impedance may actually be so low at a much larger output current should actually flow from the electrosurgical generator. For any desired output power level, a minimum voltage level signal is established which linearly relates to that desired output power level. Because the minimum voltage limit signal at 58 establishes that constant maximum output current of the surgical signal which the electrosurgical generator will deliver into low impedances the minimum voltage limit signal and the desired output power signal at 76 are linearly related. The output current will be limited to a predetermined maximum at all low impedances, regardless of power settings. This can be understood by reference to the low impedance ranges of the graphs of FIGS. 5 and 6. The output surgical power increases approximately linearly as the impedance increases in the low impedance range (up to ZL) because of the constant maximum value which the current can attain at low impedances due to the introduction of the artificial minimum voltage limit signal at 58 related to the desired power output level. The limit on the maximum output current prevents internal destruction of circuit elements of the generator, among other advantages.

The current and voltage delivered signals at 68 and 70, respectively, are applied to the input terminals of a conventional multiplier 72 as shown in FIG. 2. These signals are multiplied together and the product signal is supplied as a delivered power signal at 74 to the positive input terminal of differential amplifier 78. The desired output power signal at 76 is applied through an appropriate resistance network to the negative input terminal of the differential amplifier 78. The differential amplifier 78 supplies an error signal at 80 which is related in magnitude and sign (positive or negative) to the difference between the delivered power signal at 74 and the desired output power signal at 76. When there is a great disparity between the delivered and desired amounts of power, the magnitude of the error signal at 80 is great. When the delivered power is approximately equal to the desired power, the magnitude of the error signal at 80 is very small or substantially nonexistent. The sign of the error signal at 80 establishes whether more or less power should be supplied to achieve regulation.

The RMS to DC converters 44 and 46 are conventional items, as is the multiplier 72. RMS to DC converters which have proved satisfactory are number AD 536 AJH, manufactured by Analog Devices of Two Technology Way, P.O. Box 280, Norwood, Mass., 02062, U.S.A.

Details of the pulse width modulation circuit 82, the amplifier drive circuit 86, the RF amplifier 82 and the output transformer 26 are shown in FIG. 3. The error signal at 80 from the differential amplifier 78 (FIGS. 1 and 2) is applied to a conventional integrator defined by an op amp 134 and an integrating feedback network including the capacitor 136. The integrator has the effect of continually time integrating or averaging the error signal 80, as well as creating control loop stability. The output signal of the integrator at 138 is always a positive level trigger level signal. The sign of the error signal created by the differential amplifier 78 (FIG. 2) is coordinated with the operation of the integrator to create this positive level trigger signal. When the error signal at 80 is negative in sign, indicating a need for more power, the integration increases the magnitude of the trigger level signal at 138. When the error signal at 80 is positive in sign, indicating the need for less power, the integration decreases the magnitude of the trigger level signal at 138. When the error signal at 80 is zero or nonexistent, the magnitude of the trigger level signal at 138 remains unchanged.

The trigger level signal at 138 is presented to the base terminal of a transistor 140. Transistor 142 and transistor 140 form a discrete component comparator. The other input signal to this discrete comparator is applied at 144 to the base terminal of the transistor 142. This other input signal at 144 is that signal across capacitor 146. The transistor 148 and its associated biasing elements define a constant current source for charging the capacitor 146 at a constant current rate. Accordingly, the voltage signal across capacitor 146 increases in a linear or ramp-like fashion and thus creates a ramp signal at 144. A signal at 150 from a conventional edge detector 152 energizes the FET 154 to discharge the capacitor 146. Once discharged, the capacitor 146 immediately commences charging again.

The ramp signal at 144 across the capacitor 146 is periodic in nature, because the edge signal at 150 is periodic, and the capacitor 146 periodically discharges through the FET 154. The periodic edge signal at 150 is derived from the oscillator signal at 98 supplied from a conventional oscillator 156 which is a part of the amplifier drive circuit 86. The oscillator signal at 98 establishes the frequency for the high or radio frequency surgical signal delivered to the patient by the electrosurgical generator. The oscillator signal at 98 is shown in FIG. 4A. The edge detector 152 responds to each positive going and negative going edge of the oscillator signal and supplies a narrow pulse at each edge transition of the oscillator signal. The edge signal shown in FIG. 4D is thus a series of relatively narrow pulses, each occurring at an edge of the oscillator signal. Each pulse of the edge signal causes the FET 154 to rapidly discharge the capacitor 146. The constant current source established by the transistor 148 immediately commences charging the capacitor 146 and the voltage across the capacitor builds linearly to create the ramp signal at 144 shown in FIG. 4E. Thus, the ramp signal shown in FIG. 4E takes on the characteristics of a sawtooth wave having a frequency established by the edge signal and which is approximately twice the frequency of the oscillator signal shown in FIG. 4A.

The oscillator signal at 98 is presented to a flip-flop logic and gating circuit 160 and to the duty cycle generator 92, as shown in FIG. 3. The duty cycle generator 92 is under the control of the mode logic circuit 62 (FIG. 1) by virtue of the signals at 94, and establishes the duty cycle signal at 96 to control the delivery of the high-frequency pulses in accordance with the selected mode of operation. The duty cycle signal at 96 is referenced to and coordinated with the oscillator signal at 98 to cause the on-time and off-time periods of the duty cycle envelope to begin with and end with the oscillator cycles. So long as the duty cycle generator 92 signals at 96 for the delivery of the high-frequency surgical signal, the logic and gating circuit supplies two periodic pulse phase signals at 162 and at 164 at the predetermined high or radio frequency of the oscillator signal at 98. The two pulse phase signals are phase-shifted one hundred eighty degrees with respect to one another. A pulse phase 1 signal is present at 162 and a pulse phase 2 signal is present at 164. The width of each pulse in both the pulse phase 1 and phase 2 signals represents the maximum width to which each driving pulse at 90 (FIGS. 1 and 3) is allowed to expand to achieve power regulation. The pulse phase 1 signal and the pulse phase 2 signal are represented at FIGS. 4B and 4C, respectively.

The technique for achieving pulse width modulation by virtue of the trigger level signal at 138 can now be described. Initially, the edge signal at 150 causes the FET 154 to discharge the capacitor 146. Thereafter, the capacitor 146 commences charging and transistor 142 begins conducting. Transistor 142 continues to conduct as the voltage across capacitor 146 reaches a level equivalent to the level of the trigger level signal at 138. As soon as the voltage across capacitor 146, i.e., the ramp signal at 144, increases slightly over the trigger level signal, transistor 140 commences conducting and transistor 142 stops conducting, because the voltage on the base terminal of transistor 142 has exceeded the voltage at the base terminal of transistor 140. Once transistor 140 commences conducting a termination signal is present at 166 across resistor 168 and at the base of transistor 170. The termination signal at 166 is illustrated in FIG. 4G.

The effects of the trigger level signal at 138 in controlling the ramp signal at 144 due to the action of the discrete component comparator formed by transistors 140 and 142, is illustrated in FIG. 4F. As soon as the ramp signal increases to a level equivalent to the trigger level signal, the termination signal shown in FIG. 4G is delivered. The width of each pulse of the termination signal is that remaining time portion of each interval of the ramp signal (FIG. 4E) before discharge the capacitor 146 and the commencement of the next individual ramp of the ramp signal. The high portion of the termination signal at 166 biases the transistor 170 into conduction.

The pulse width control signal at 84 is created by the switching effects of transistor 170. The signal level at 84 immediately drops when transistor 170 begins conducting due to the effects of the resistor 174. When transistor 170 is not conducting, the level of the signal at 84 is high. The pulse width control signal is illustrated in FIG. 4H. The pulse width control signal is the inversion of the termination signal shown in FIG. 4G.

The pulse width control signal at 172 is applied to one input terminal of both AND gates 176 and 178. The pulse phase 1 signal at 162 is applied to the other input terminal of the AND gate 176 and the pulse phase 2 signal at 164 is applied to the other input terminal of another AND gate 178. AND gates 176 and 178 supply high output signals at 180 and 182, respectively, so long as both input signals are high. A pulse width modulated phase 1 signal is present at 180 upon the existence of the high level of the pulse phase 1 signal at 162 and the existence of high level of the pulse width control signal at 84. The pulse width modulated phase 1 signal at 180 goes to a low level when the pulse width control signal at 84 drops to a low level. Accordingly, the time width of the pulse width modulated phase 1 signal is controlled or modulated by the pulse width control at 84. This is illustrated by considering that the signals shown in FIGS. 4B and 4H are both at high levels during the time that the pulse width modulated phase 1 signal shown in FIG. 4I is delivered. As soon as the pulse width control signal shown in FIG. 4H goes low, the pulse width modulated phase 1 signal also goes low. A similar situation exists with respect to the pulse width modulated phase 2 signal at 182. The AND gate 178 gates the pulse phase 2 signal at 164 (FIG. 4C) with the pulse width control signal at 84 (FIG. 4H). The width of each pulse width modulated phase 2 signal at 182 terminates when the pulse width control signal goes low. The pulse width modulated phase 2 signal is shown in FIG. 4J and is derived by considering FIGS. 4C and 4H in the logical manner established by operation of the AND gate 178.

It should be noted that the edge signal at 150 controls the FET 184 simultaneously with the FET 154. When the FET 184 is conductive, the signal level at 166 drops approximately to reference level and the conduction of transistor 170 terminates. Thus, conduction of the FET 184 assures that the pulse width control signal at 84 commences each pulse width determination period at a high level and also assures that transistor 142 is conducting at the beginning of each pulse width determination period.

As has been described, the error signal at 80 and the trigger level signal at 138 operatively control the width of each pulse width modulated phase 1 and phase 2 signal at 180 and 182, respectively. When the error signal at 84 is substantially large in a negative sense, indicating the need for great power, the ramp signal (FIG. 4E) present at 144 will not reach the relatively large magnitude of the trigger level signal, in contrast to that situation shown in FIG. 4F. Hence, substantially full width pulse width modulated phase 1 and phase 2 signals will be delivered at 180 and 182 because the transistor 140 will not become conductive. The edge signal at 150 will cause capacitor 146 to discharge before transistor 140 ever becomes conductive. Since transistor 140 never becomes conductive, the pulse width control signal at 84 remains continually high and the width of each pulse of the pulse width modulated phase 1 and phase 2 signals at 180 and 182, respectively, is driven to the full width of the pulse phase 1 and pulse phase 2 signals at 162 and 164, respectively. Accordingly, FIGS. 4B and 4C also respectively represent the full width pulse width modulated phase 1 and phase 2 signals present both at 180 and 182. As soon as power builds up and the error signal 80 decreases to zero, the level of the trigger level signal attains desired power regulation because the width of the pulses is established to secure the desired amount of power delivery. If the electrosurgical generator is delivering an excessive amount of power, the error signal at 80 becomes positive. The integration of the positive error signal reduces the magnitude or level of the trigger level signal at 138, thus causing the pulse width control signal (FIG. 4H) to drop to a low level at an earlier point in each full phase time period. Accordingly, the width of each pulse width modulated phase 1 and phase 2 signal is reduced and the amount of output power is thus reduced.

In addition to those functions of the flip-flop logic and gating circuit 160 previously described, the flip-flop logic and gating circuit also includes conventional gating circuit elements (not shown) for assuring that pulse width modulated phase 1 signal at 180 is delivered first, followed by a pulse width modulated phase 2 signal at 182. In addition, when the duty cycle generator 92 calls for the termination of the surgical signal, the logic and gating circuit 160 assures that the on time of the duty cycle envelope terminates after a pulse width modulated phase 2 signal has been delivered. All of the functions of the flip-flop logic and gating circuit 160 can be achieved by the interconnection of binary logic elements, primarily flip-flops and gates.

Each of the pulse width modulated phase 1 and phase 2 signals at 180 and 182, respectively, is applied to its own phase drive circuit. One phase drive circuit is illustrated at 186. The phase drive circuits for both the pulse width modulated phase 1 and phase 2 signals are the same as that single one illustrated at 186. Accordingly, a description of the operation of the phase drive circuit 186 is made below with respect to a pulse width modulated phase signal P, although it should be understood that both the pulse width modulated phase 1 and phase 2 signals have the same effect on their respective phase drive circuits as the phase signal P has on the phase drive circuit 186.

The phase signal P is applied at 18S to the phase drive circuit 186 and causes FET 190 to become conductive. A transformer 192 includes a center tapped primary winding and the coil 194 thereof is poled to induce a positive signal at terminal 196 with respect to terminal 198 and a positive signal at terminal 200 with respect to terminal 202. The terminals 196 and 200 are connected to FET's Q1A and Q1B of the RF amplifier 22. The positive signals at 196 and 200 turn on both FET's Q1A and Q1B and causes current to be conducted at 20 from the DC power supply 16 (FIG. 1) through the primary winding of the power output transformer 26. Whenever the phase signal P terminates, a narrow reset pulse $\bar{P}$ goes high at conductor 204. The reset pulse signal $\bar{P}$ is created by the negative going edge of the phase signal P. FET 206 becomes conductive and current is momentarily conducted in the reverse direction in the primary winding coil 208 of the transformer 192. The narrow reverse pulse of current in the primary winding coil 208 resets the magnetics or hysteresis characteristics of the core of the transformer 192 to ready it for conduction during the next phase signal P. The various signals at terminals 196, 198, 200 and 202 are illustrative of those comprising, collectively, the drive signal at 90.

The other one of the two pulse width modulated phase signals at 180 or 182 has a corresponding effect on its phase drive circuit and the FET's Q2A and Q2B are rendered conductive and nonconductive in the same manner as has been previously described. When FET Q2A and Q2B are conductive, the direction of current flow through the primary winding of the power output transformer 26 reverses. Accordingly, an alternating current pulse width modulated signal at 28 is created by the drive signal applied to the amplifier 22. Examples of the alternating pulse width modulated signal at 24 are shown in FIGS. 4K and 4L.

The alternating pulse width modulated signal to the primary winding of the power output transformer 26 for full-width driving pulses of the drive signal at 90 is illustrated in FIG. 4K. In the waveform shown in FIG. 4K, it is to be noted that the full-width pulse width modulated phase 1 signal (e.g., FIG. 4B) creates the positive portion of the signal and the full-width pulse width modulated phase 2 signal (e.g., FIG. 4C) creates the negative portion of the transformer input signal. For less-than-full-width driving pulses of the drive signal, the waveform presented to the primary winding of the power output transformer is shown in FIG. 4L. Again, the pulse width modulated phase 1 signal (FIG. 4I) creates the positive portion while the pulse width modulated phase 2 signal (FIG. 4J) creates the negative portion. It is to be noted that the waveform shown in FIG. 4L has the frequency characteristic exactly the same as the frequency characteristic of the oscillator signal (FIG. 4A).

The amount of energy delivered by the AC pulse modulated signal at 28 from the power transformer 26 is defined generally by the area above and below the zero reference point of the waveforms shown in FIGS. 4K and 4L, although the AC pulse modulated signal at 28 will not actually have the square pulse shapes shown due to the inductive effects of the filter 30 which are reflected back to the primary winding of the transformer 26. This energy is presented at a periodic basis at the band pass frequency of the band pass filter 30 (FIG. 1). Accordingly, the band pass filter is driven at its band pass frequency to deliver the sinusoidal surgical signal shown in FIG. 4M at the predetermined high frequency. The passive reactive elements of the band pass filter 30 change the AC pulse modulated signal at 28 into sinusoidal oscillations. Each cycle of the sinusoidal surgical signal is created by and correspondingly results from one cycle (a positive and negative pulse) of the pulse width modulated signal at 24, e.g., FIGS. 4K and 4L. The relationship and correspondence between the pulse width modulated signal at 24 and the sinusoidal surgical signal at 32 is illustrated by comparing FIG. 4M to FIGS. 4K and 4L. When a full-width pulse-width-modulated signal is received, such as that shown in FIG. 4K, the amplitude of the sinusoidal surgical signal will be greater than when a less-than-full-width pulse-width-modulated signal, such as that shown in FIG. 4L, is supplied for the same impedance load. Thus, the power of the surgical signal present on conductor 32 is defined by the area or width of the pulse width modulated phase 1 and phase 2 signals and the corresponding pulses of the drive signal which drive and control the switching of the amplifier 22.

One of the advantages of regulating both the output of the DC power supply 16 by the control signal at 18, shown in FIG. 1, and by pulse width modulation as described herein is that the pulse width modulation obtains a better resolution (i.e., allows expansion to substantially the major portion of the pulse width) for given power settings. In other words, the DC power supply 16 (FIG. 1) generally or coarsely regulates the amount of power and the pulse width modulation capability of the present invention achieves a finally regulated and rapid control over the amount of power actually delivered. The inherent maximum power delivery capacity of the power supply is limited by this approach, however, and relatively rapid power roll-off occurs at higher output impedances.

The pulse width modulation power regulation technique described herein allows the energy content of each cycle of the sinusoidal output wave applied to the patient to be energy regulated. Very precise power regulation occurs. Very rapid response times are also possible to achieve greatly improved constant power regulation when the tissue impedance rapidly fluctuates. Superior and greatly improved surgical effects result. The constant power regulation available from the present invention even into relatively high impedance tissues is a substantial improvement in the field of electrosurgery. Limiting the maximum output voltage at high impedances in the manner described herein avoids or reduces the possibility for flash and undesirable arcing, as well as reducing the risk of alternate path burns to the patient. Limiting the maximum output current at low impedances to a predetermined maximum at any particular power setting avoids the possibility of destruction to the electrosurgical generator as a result of short circuiting the output electrodes or terminals. Numerous other improvements and advantages of the present invention have been discussed above or will be apparent after full comprehension of the present invention.

A preferred embodiment of the present invention has been shown and described with a degree of particularity. It should be understood, however, that the specificity of the present description has been made by way of preferred example, and that the scope of the present invention is defined by the appended claims.

What is claimed is:

1. In a electrosurgical generator including means for supplying a surgical signal at a predetermined high frequency to perform a surgical procedure, and means for regulating the power content of the surtgical signal, and an improved feedback means for controlling the power regulating means comprising:
    means for creating a current delivered signal related to the current of the surgical signal;
    means for establishing a current limit signal;
    voltage limit means receptive of the current limit signal and the current delivered signal and operative for supplying a first signal corresponding to one of either the current limit signal or the current delivered signal, said voltage limit means operatively supplying the current delivered signal as the first signal when the current delivered signal is greater than the current limit signal and operatively supplying the current limit signal as the first signal when the current delivered signal is less than the current limit signal;
    means for creating a voltage delivered siganl related to the voltage of the surgical signal;
    means for establishing a voltage limit signal;
    curret limit means receptive of the voltage limit signal and voltage delivered signal and operative for supplying a second signal corresponding to one of either the voltage limit signal or the voltage delivered signal, said current limit means operatively supplying the voltage delivered signal as the second signal when the voltage delivered signal is greater than the voltage limit signal and operatively supplying the voltage limit signal as the second signal when the voltage delivered signal is less than the voltage limit signal;
    multiplier means receptive of the first and second signals and operative for multiplying the first and second signals to create a delivered power signal which is the product of the first and second signals; and
    means receptive of the delivered power signal and operative for controlling the power regulation means of said generator to regulate the power content of the surgical signal in response to the power delivered signal.

2. In an elcctrcsurgical generator as defined in claim 1, the current delivered signal is directly related to the RMS current of the surgical signal, and the voltage delivered signal is directly related to the RMS voltage of the surgical signal.

3. In an electrosurgical generator as defined in claim 1, at least one of the limit signals received by said limit means is of a constant value.

4. In an electrosurgical generator as defined in claim 3, the current delivered signal is directly related to the RMS current of the surgial signal, and the voltage delivered signal is directly related to the RMS voltage of the surgical signal.

5. In an electrosurgical generator as defined in claim 1, said improved feedback means further comprises:
    means for supplying a desired output power signal representative of a predetermined amount of power which the surgical signal is desired to contain;
    differential means receptive of the delivered power signal and the desired output power signal and operative for creating an error signal representative of the difference of the delivered power signal with respect to the desired output power signal; and wherein:
    said means for controlling the power regulation means does so in predetermined relation to the error signal.

6. In an electrosurgical generator as defined in claim 5, at least one of the limit signals received by said limit means is related to the desired output power signal.

7. In an electrosurgical generator as defined in claim 6, the current delivered signal is directly related to the RMS current of the surgical signal, and the voltage delivered signal is directly related to the RMS voltage of the surgical signal.

8. In an electrosurgical generator as definned in claim 6, the one limit signal received by said limit means is non-linearally related to the desired output power signal.

9. In an electrosurgical generator as defined in claim 6, the current delivered signal is directly related to the RMS current of the surgical signal, and the voltage delivered signal is directly related to the RMS voltage of the surgical signal.

10. In an electrosurgical generator as defined in claim 1, said surgical signal is a series of substantially sinusoidally shaped cycles occurring at the predetermined high frequency, and a further improvement in said means for supplying the surgical signal comprises:
    drive means for creating a periodic series of driving pulses occurring at a predetermined frequency which is related to the predetermined high frequency of the surgical signal, each driving pulse having a predetermined energy content related to the time width of the driving pulse; and
    surgical signal creating means receptive of the driving pulses for creating the surgical signal from the driving pulses, said creating means creating each cycle of the surgical signal from at least one corresponding driving pulse, said creating means further establishing an energy content of each cycle of the surgical signal in a direct relationship to the energy content of each corresponding driving pulse from which the cycle of the surgical signal was created.

11. In an electrosurgical generator as defined in claim 10, the predetermined frequency at which the driving pulses occur is twice the predetermined high frequency of the surgical signal, alternate driving pulses in the periodic series primarily create a positive half cycle of each cycle of the surgical signal and the other alternate driving pulses primarily create the negative half cycle of each cycle of the surgical signal, and sequential driving pulses alternate in polarity with respect to one another.

12. In an electrosurgical generator as defined in claim 11, said means for supplying the surgical signal further comprises:

bandpass filter means receptive of the driving pulses and operative for converting the driving pulses into the substantially sinusoidally shaped cycles of the surgical signal at the predetermined high frequency, said bandpass filter means operatively changes the amplitude of the substantially sinusoidally shaped cycles of the surgical signal in a predetermined relationship to the width of each driving pulse creating the cycle of the surgical signal.

13. An electrosurgical generator which supplies a surgical signal having a series of substantially sinusoidually shaped cycles occurring at a fixed predetermined radio frequency, comprising:

drive means for creating a periodic series of driving pulses occurring at a predetermined frequency related to the predetermined radio frequency of the surgical signal, each driving pulse having a predetermined energy content related to the time width of the driving pulse;

surgical signal creating means receptive of the driving pulses for creating the surgical signal from the driving pulses, said creating means creating each cycle of the surgical signal from at least one corresponding driving pulse, said creating means further establishing an energy content of each cycle of the surgical signal in a direct relationship to the energy content of each corresponding driving pulse from which the cycle of the surgical signal was created;

means responsive to the surgical signal and operative for creating a delivered power signal related to the power content of the surgical signal;

means for establishing a desired output power signal related to a desired amount of output power for the surgical signal; and means receptive of the delivered power signal and the desired output power signal and operative for modulating the width of the driving pulses in accordance with a predetermined relationship of the delivered power signal and the desired output power signal to regulate the power content of the surgical signal.

14. An electrosurgical generator as defined in claim 13, wherein the energy content of each cycle of the surgical signal is established by varying the amplitude of the sinusoidal shaped cycle.

15. An electrosurgical generator as defined in claim 13 further comprising:

bandpass filter means receptive of the driving pulses and operative for converting the driving pulses into the substantially sinusoidally shaped cycles of the surgical signal at the predetermined radio frequency.

16. An electrosurgical generator as defined in claim 15 wherein:

said bandpass filter means operatively changes the amplitude of the substantially sinusoidally shaped cycles of the surgical signal in a predetermined relationship to the width of each driving pulse creating the cycle of the surgical signal.

17. An electrosurgical generator as defined in claim 16 wherein:

said bandpass filter means primarily creates each half cycle of each substantially sinusoidally shaped cycle of the surgical signal from a corresponding drivig pulse of the periodic series of driving pulses.

18. An electrosurgical generator as defined in claim 16 wherein:

the predetermined frequency at which the driving pulses occur is twice the predetermined radio frequency of the surgical signal, alternate driving pulses of the periodic series primarily create a positive half cycle of each cycle of the surgical signal and the other alternate driving pulses of the periodic series create the negative half cycle of each cycle of the surgical signal, and sequential driving pulses of the periodic series alternate in polarity with respect to one another.

19. An electrosurgical generator as defined in claim 13 further comprising:

means for creating one of a current sensed signal or a voltage sensed signal related to the current or the voltage content of the surgical signal supplied by the electrosurgical generator, respectively;

means for establishing one of a current limit signal or a voltage limit signal;

limit means receptive of the one limit signal and the one sensed signal which have the same current or voltage relationship and operative for supplying the sensed signal as a delivered signal when the one sensed signal occupies a first predetermined relationship to the one limit signal and operative for supplying the limit signal as the delivered signal when the one sensed signal occupies a second predetermined different relationship to the one limit signal; and and wherein said modulating means modulates the width of the driving pulses in relation to the delivered signal.

20. An electrosurgical generator as defined in claim 19 wherein the one limit signal established is of a constant value.

21. An electrosurgical generator as defined in claim 19 wherein the one limit signal established is non-linearly related to a desired amount of output power to which the surgical signal is to be regulated.

22. An electrosurgical generator as defined in claim 19 wherein the one limit signal established is linearly related to a desired amount of output power to which the surgical signal is to be regulated.

23. An electrosurgical generator as defined in claim 13 wherein the delivered power signal is related to the instantaneous RMS power content of the surgical signal.

24. An electrosurgical generator which supplies a predetermined surgical signal to perform a surgical procedure and which regulates the power content of the surgical signal, the surgical signal being a series of individual cycles occurring at a predetermined radio frequency, said generator comprising:

drive means for creating a drive signal defined by a periodic series of driving pulses occurring at a predetermined frequency and time relationship with respect to each cycle of the radio frequency surgical signal, each driving pulse having a predetermined energy content related to the time width of the driving pulse;

surgical signal creating means receptive of the driving pulses for creating the surgical signal from the driving pulses, said creating means creating each cycle of the surgical signal from at least one corresponding driving pulse, said creating means further establishing an energy content of each cycle of the surgical signal in a direct relationship to the energy content of each corresponding driving pulse from which the cycle of the surgical signal was created;

means for creating a current delivered signal related to the RMS current of the surgical signal;

means for establishing a current limit signal;

voltage limit means receptive of the current limit signal and the current delivered signal and operative for supplying a first signal corresponding to one of either the current limit signal or the current delivered signal, said voltage limit means operatively supplying the current delivered signal as the first signal when the current delivered signal is greater than the current limit signal and operatively supplying the current limit signal as the first signal when the current delivered signal is less than the current limit signal;

means for creating a voltage delivered signal related to the RMS voltage of the surgical signal;

means for establishing a voltage limit signal;

current limit means receptive of the voltage limit signal and voltage delivered signal and operative for supplying a second signal corresponding to one of either the voltage limit signal or the voltage delivered signal, said current limit means operatively supplying the voltage delivered signal as the second signal when the voltage delivered signal is greater than the voltage limit signal and operatively supplying the voltage limit signal as the second signal when the voltage delivered signal is less than the voltage limit signal;

multiplier means receptive of the first and second signals and operative for multiplying the first and second signals to create a delivered power signal which is the product of the first and second signals;

means for supplying a desired output power signal representative of a predetermined amount of power which the surgical signal is desired to contain;

differential means receptive of the delivered power signal and the desired output power signal and operative for creating an error signal representative of the difference of the delivered power signal with respect to the desired output power signal; and modulation means receptive of the error signal and operative for controlling said drive means to modulate the width of each driving pulse in a predetermined relation to the error signal, said modulation means operatively changing the predetermined energy content of each driving pulse to regulate the energy content of each cycle of the surgical signal to a level related to the power level represented by the desired output power signal.

25. A electrosurgical generator as defined in claim 24 wherein said modulation means further comprises:

integrator means receptive of the error signal and operative for integrating the error signal over time and creating a trigger level signal related to the integrated value of the error signal;

means for creating a ramp signal having a periodic series of ramp waveforms occurring at a predetermined frequency related to the frequency of the driving pulses;

comparator means receptive of the ramp signal and the trigger level signal and operative for creating a pulse width control signal having a characteristic occurring periodically at the predetermined frequency of the ramp signal, the pulse width control signal operatively controlling the width of each driving pulse.

26. An electrosurgical generator as defined in claim 25 wherein said drive means further comprises:

pulse phase means for creating a pulse phase signal having a periodic series of phase pulses occurring at the predetermined frequency of said driving pulses; and gating means receptive of the pulse phase signal and the pulse width control signal and operative for creating each driving pulse having a time width related to the phase pulse signal and the periodic characteristic of the pulse width control signal.

27. An electrosurgical generator as defined in claim 26 wherein each phase pulse signal has a predetermined time width and the width of each phase pulse signal defines the maximum possible width of each driving pulse.

28. An electrosurgical generator as defined in claim 27 wherein:

said gating means operatively initiates each driving pulse in relation to the occurrence of each phase pulse and operatively terminates each driving pulse in relation to the occurrence of the periodic characteristic of the pulse width control signal.

29. An electrosurgical generator as defined in claim 26 wherein:

said pulse phase means creates a pulse phase one signal and a pulse phase two signal which are phase shifted with respect to one another by one hundred eighty degrees, both the pulse phase one signal and the pulse phase two signal having the characteristics of the aforesaid pulse phase signal;

the predetermined frequency of the ramp waveforms of the ramp signal and of the periodic characteristic of the pulse width control signal are two times the frequency of the surgical signal; and said gating means is receptive of the pulse phase one signal and the pulse phase two signal and operatively creates individual phase one driving pulses in relation to the phase one pulse signal and the periodic characteristic of the pulse width control signal and operatively creates individual phase two driving pulses in relation to the phase two pulse signal and the periodic characteristic of the pulse width control signal, each phase one driving pulse and each phase two driving pulse having the characteristics of each aforesaid driving pulse, the phase one driving pulses and the phase two driving pulses defining the drive signal.

30. An electrosurgical generator as defined in claim 29 wherein:

said surgical signal creating means receptive of the driving pulses and operative for creating each cycle of the surgical signal operatively creates one half-cycle of each cycle of the surgical signal from a phase one driving pulse and operatively creates the other half-cycle of each cycle of the surgical signal from a phase two driving pulse.

31. An electrosurgical generator as defined in claim 24 wherein each cycle of the surgical signal is substantially sinusoidally shaped and said surgical signal creating means further comprises:

bandpass filter means receptive of the driving pulses and operative for converting the driving pulses into the substantially sinusoidally shaped cycles of the surgical signal at the predetermined radio frequency.

32. An electrosurgical generator as defined in claim 31 wherein:

said bandpass filter means substantially inhibits frequency components of the driving pulses at other than the predetermined radio frequency.

33. An electrosurgical generator as defined in claim 31 wherein:
said bandpass filter means operatively changes the amplitude of the substantially sinusoidally shaped cycles of the surgical signal in a predetermined relationship to the width of each driving pulse creating the cycle of the surgical signal.

34. An electrosurgical generator as defined in claim 31 wherein:
said bandpass filter means primarily creates each half cycle of each substantially sinusoidally shaped cycle of the surgical signal from one corresponding driving pulse.

* * * * *